United States Patent [19]
Griffith et al.

[11] Patent Number: 5,455,259
[45] Date of Patent: * Oct. 3, 1995

[54] COMPOUNDS FOR THE TREATMENT OF NEURODEGENERATIVE DISORDERS

[75] Inventors: Ronald C. Griffith, Pittsford; Robert J. Murray, Brighton; Michael Balestra, Rochester; Donald Mathisen, Fairport, all of N.Y.

[73] Assignee: Fisons Corporation, Rochester, N.Y.

[ * ] Notice: NOTE-DISCLAIMER The portion of the term of this patent subsequent to Jul. 4, 2012 has been disclaimed.

[21] Appl. No.: 221,076

[22] Filed: Mar. 31, 1994

Related U.S. Application Data

[60] Continuation-in-part of Ser. No. 915,489, Jul. 16, 1992, which is a division of Ser. No. 427,661, Oct. 27, 1989, abandoned, which is a continuation-in-part of Ser. No. 232,566, Aug. 12, 1988, abandoned, which is a continuation-in-part of Ser. No. 11,982, Feb. 6, 1987, abandoned.

[30] Foreign Application Priority Data

Apr. 1, 1993 [WO] WIPO ............... PCT/GB93/00689
Oct. 1, 1993 [GB] United Kingdom ............... 9320273

[51] Int. Cl.$^6$ .................. A61K 31/44; C07D 213/36
[52] U.S. Cl. ................................ 514/357; 546/329
[58] Field of Search ............... 546/329; 514/357

[56] References Cited

U.S. PATENT DOCUMENTS

| | | | |
|---|---|---|---|
| 3,420,841 | 1/1969 | Brust et al. | 546/337 |
| 3,510,560 | 5/1970 | Saunders | 546/337 |

FOREIGN PATENT DOCUMENTS 0356035  2/1990  European Pat. Off. .

OTHER PUBLICATIONS

Niemers et al, CA:86–106314w, 1977.
Shimada et al, CA:102–166589v, 1985.
Medical Subject Headings—Tree Structures, 1992 (1975, 1969).
J. B. Taylor, "Comprehensive medicinal chemistry, vol. 5, Biopharmaceutics" p. 379, lines 9–13, 1990.

Primary Examiner—Richard L. Raymond
Assistant Examiner—Deborah Lambkin
Attorney, Agent, or Firm—McAulay Fisher Nissen Goldberg & Kiel

[57] ABSTRACT

(S)-α-phenyl-2-pyridineethanamine, and its pharmaceutically acceptable derivatives, are useful in the treatment of neurodegenerative disorders, and exhibit linear pharmacokinetics.

18 Claims, No Drawings

COMPOUNDS FOR THE TREATMENT OF NEURODEGENERATIVE DISORDERS

CROSS-REFERENCE TO RELATED APPLICATIONS

This application is a continuation-in-part of U.S. patent application Ser. No. 07/915,489, filed Jul. 16, 1992, which is a divisional of U.S. patent application Ser. No. 07/427,661, filed Oct. 27, 1989, now abandoned, which, in turn, is a continuation-in-part of U.S. patent application Ser. No. 07/232,566, filed Aug. 12, 1988, now abandoned, which, in turn, is a continuation-in-part of U.S. patent application Ser. No. 07/011,982, filed Feb. 6, 1987, now abandoned, the contents of which are incorporated by reference.

BACKGROUND OF THE INVENTION

This invention relates to an enantiopure (S)-enantiomer of a compound known to exist as a racemate, its use as a pharmaceutical, in particular in the treatment of neurodegenerative disorders, a process for its production, and pharmaceutical formulations including the enantiomer.

A major problem with existing drugs used to treat neurodegenerative disorders is a lack of predictability in the concentration of a drug in a patient's blood plasma resulting from administration of a given quantity of that drug, i.e. existing drugs do not exhibit linear pharmacokinetics. It has been stated that an ideal drug in this field would show a linear relationship between blood plasma concentration and dose size so that a given change in dose would yield a predictable change in blood plasma concentration of the drug ['Pharmacokinetics of old, new and yet-to-be discovered antiepileptic drugs', R H Levy and B M Kerr, Epilepsia, vol 30, Supp 1, S35–S41, 1989].

Parent application Ser. No. 07/915,489 discloses compounds for use in the treatment of neurodegenerative disorders, having the formula $$Ar_1-CH_2-\underset{NR_2R_3}{\overset{R_1}{\underset{|}{\overset{|}{C}}}}-Ar_2 \quad (I)$$

wherein $Ar_1$ and $Ar_2$, which may be the same or different, independently represent phenyl substituted by one or more of amino, nitro, chlorine, bromine, hydroxy, C1 to 6 alkoxy, C1 to 6 alkyl or cyano; in addition one of $Ar_1$ or $Ar_2$ may also represent phenyl;

$R_1$ represents hydrogen or C1 to 6 alkyl;

$R_2$ represents hydrogen or $COCH_2NH_2$;

$R_3$ represents hydrogen or C1 to 6 alkyl; provided that when $R_2$ represents hydrogen, then one or both of $Ar_1$ and $Ar_2$ may also represent phenyl, fluorophenyl or 2-, 3- or 4-pyridinyl and $R_1$ may also represent C1 to 6 alkoxycarbonyl or trifluoromethyl; or a pharmaceutically acceptable salt thereof.

Included in these compounds is α-phenyl-2-pyridineethanamine [referred to therein as 1-phenyl-2-(2-pyridinyl)ethylamine],

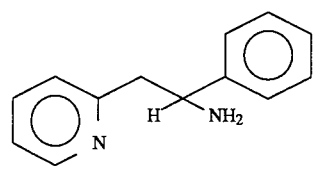

SUMMARY OF THE INVENTION

Surprisingly, we have now discovered that the (S)-enantiomer of this compound exhibits linear pharmacokinetics, whereas the racemate exhibits nonlinear pharmacokinetics.

Thus, according to the present invention, there is provided (S)-α-phenyl-2-pyridineethanamine,

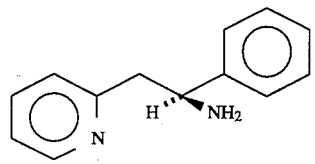

substantially free from its (R)-enantiomer, and pharmaceutically acceptable derivatives thereof (hereinafter referred to together as "the compounds of the invention").

By "substantially free from its (R)-enantiomer", is meant that a sample of the (S)-enantiomer contains less than 10% by weight of the (R)-enantiomer (i.e. it is more than 90% enantiopure), more preferably less than 1% by weight of the (R)-enantiomer, and most preferably as little of the (R)-enantiomer as known methods of optical purification (e.g. fractional crystallization, chiral chromatography), chiral starting materials and/or chiral synthesis will allow.

Pharmaceutically acceptable derivatives include compounds which are suitable bio-precursors (prodrugs) of (S)-α-phenyl-2-pyridineethanamine, including the acid addition salts, which are of particular interest.

Suitable bioprecursors of (+)-α-phenyl-2-pyridineethanamine include amino acid amide derivatives of the amino group, in particular α-amino acid derivatives such as glycine derivatives. Such derivatives may be prepared by conventional methods, for example amino acid amide derivatives may be prepared by the methods given in 'Advanced Organic Chemistry' by J March, 2nd edition, published by McGraw-Hill, page 1171.

Acid addition salts of (S)-α-phenyl-2-pyridineethanamine include salts of mineral acids, for example the dihydrochloride and dihydrobromide salts; and salts formed with organic acids such as formate, acetate, malate, benzoate and fumarate salts.

We have discovered that the (S)-malate and benzoate salts of (S)-α-phenyl-2-pyridineethanamine possess a number of advantages, including outstanding stability to moisture.

Thus, the invention further provides (S)-α-phenyl-2-pyridineethanamine (S)-malate,

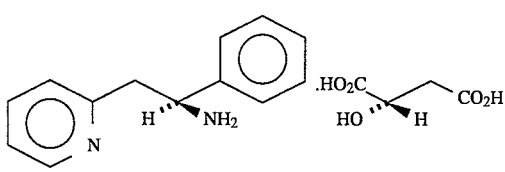

which is greater than 90% enantiopure.

In relation to this salt "greater than 90% enantiopure" means that each enantiomeric component is greater than 90% enantiopure, i.e. each enantiomeric component contains less than 10% by weight of the corresponding (R)-enantiomer.

Preferably, the (S)-malate salt is more than 99% enantiopure, most preferably as close to 100% enantiopure as known methods of optical purification (e.g. fractional crystallization, chiral chromatography), chiral starting materials and/or chiral synthesis will allow.

The invention further provides (S)-α-phenyl-2-pyridineethanamine benzoate,

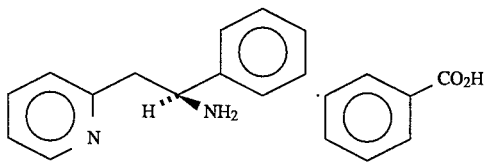

which is greater than 90% enantiopure.

By "greater than 90% enantiopure" we mean that the amine component of the salt is greater than 90% enantiopure, i.e, it contains less than 10% by weight of the corresponding (R)-enantiomer.

Preferably, the benzoate salt is more than 99% enantiopure, most preferably as close to 100% enantiopure as known methods of optical purification (e.g. fractional crystallization, chiral chromatography), chiral starting materials and/or chiral synthesis will allow.

DETAILED DESCRIPTION OF THE INVENTION

α-Phenyl-2-pyridineethanamine may be prepared by conventional methods (for example, addition of the anion of 2-picoline to N-trimethylsilyl-benzaldimine). (S)-α-phenyl-2-pyridineethanamine may then be prepared by one or more selective precipitations of a diastereomeric salt formed by reaction of α-phenyl-2-pyridineethanamine with a chiral salt, followed by one or more recrystallizations. The compound may be prepared by selective precipitation of a diastereomeric salt formed between α-phenyl-2-pyridineethanamine and a chiral acid. Chiral acids which may be mentioned include D- or L-tartaric acids and in particular S(+)- and R(−)-mandelic acids. The precipitation may be carried out in an organic solvent which does not adversely affect the reaction (for example ethyl acetate), at or around room temperature.

The inventive (S)-α-phenyl-2-pyridineethanamine (S)-malate may be prepared by:
(a) precipitation from a solution of a mixture of α-phenyl-2-pyridineethanamine, or a salt thereof, and (S)-malic acid which is greater than 90% enantiopure; or
(b) precipitation from a solution of a mixture of (S)-α-phenyl-2-pyridineethanamine, or a salt thereof, and (S)-malic acid which is greater than 90% enantiopure.

The inventive benzoate salt may be prepared by precipitation from a solution of a mixture of (S)-α-pyridineethanamine, or a salt thereof, which is greater than 90% enantiopure, and benzoic acid.

Enantiopurities may be determined by methods well known to those skilled in the art. For example, the enantiomers to be analyzed may be passed through a chiral chromatography column in normal or reverse phase mode (e.g. a Diacel Chiralcel OD column or a Diacel Chiralcel OD-R column, respectively). Also, the enantiomers to be analyzed may be derivatized with a chiral derivatizing agent [e.g. (R)- or (S)-methylbenzyl isocyanate for an amine] and passed through a chiral chromatography column (e.g. a Pirkle covalent naphthylalanine column).

The compounds of the invention are indicated as pharmaceuticals, in particular as anticonvulsants and neuroprotective agents in the treatment of neurodegenerative disorders. Specific neurodegenerative disorders that may be mentioned include stroke, cerebral ischaemia, cerebral palsy, the effects of hypoglycaemia, epilepsy, AIDS-related dementia, Alzheimer's disease, Huntington's chorea, Olivo-ponto-cerebellar atrophy, perinatal asphyxia, Parkinson's disease, anoxia, neuronal damage associated with substance abuse (for example, narcotics or cocaine), retinopathies, schizophrenia, ischaemic states after cardiac arrest or surgical operations, intoxication or injuries of the spinal cord and amyotrophic lateral sclerosis. Anticonvulsant therapy in epilepsy, and neuroprotective therapy in stroke, cerebral ischaemia and anoxia are of particular interest.

While not being limited by theory, neurodegeneration is thought to be caused or accelerated by certain excitatory amino acids found naturally in the central nervous system (CNS). Glutamate is an endogenous amino acid which has been characterized as a fast excitatory transmitter in the mammalian brain. Glutamate is also known as a powerful neurotoxin capable of killing CNS neurons under certain pathologic conditions which accompany stroke and cardiac arrest. It has been shown that the sensitivity of central neurons to hypoxia and ischaemia can be reduced by the specific antagonism of post synaptic glutamate receptors. Glutamate is characterized as a broad spectrum agonist having activity at four neuronal excitatory amino acid receptor sites. These receptor sites are named after the amino acids which selectively excite them: kainate (KA), N-methyl-D-aspartate (NMDA), quisqualate (QUIS) and 2-amino-4-phosphonobutyrate (APB). Glutamate is believed to be a mixed agonist capable of binding to and exciting all four receptor types. Thus, agents which selectively block or antagonise the action of glutamate at these receptors can prevent neurotoxic injury associated with anoxia, hypoxia or ischemia. In particular, compounds which bind to the NMDA receptor site and selectively block the action of glutamate are useful in the prevention and treatment of neurodegenerative diseases.

The pharmacological activity of the compounds of the invention may be measured in the tests set out below.
a) NMDA blocking activity is measured by assessing a compound's ability to protect mice from convulsions induced by intravenous administration of 150 mg/kg of NMDA according to the procedures of Czuczwar et al, (Neurotransmitters, Seizures and Epilepsy III, edited by G Nistico et al, Raven Press, New York 1986, pages 235–246). Groups of mice are pretreated by 30 minutes with the test compound by the intraperitoneal route and then given NMDA. Animals are observed for convulsions as defined by loss of righting reflex and appearance of tonic/clonic seizures. Animals are kept for 60 minutes after NMDA dosing and mortality is recorded.

b) NMDA receptor antagonist activity may be measured in vitro by assaying a compound's ability to inhibit binding of the receptor antagonist 10,11-dihydro-5-methyl-5H-dibenzo [a,d]-cyclohepten-5,10-imine (MK 801) to the receptor. The method is described by Foster and Wong, Br J Pharmacol 91, 403–409 (1987).

c) NMDA and glycine receptor affinity may also be tested in the [$^3$H]L-glutamate and [$^3$H]glycine binding assays following the method of Monaghan & Cotman, PNAS, 83, 7532, (1986) and Watson et al, Neurosci Res Comm, 2, 169, (1988).

d) Antihypoxia activity may be measured conveniently in mice. Groups of mice are tested at various times after the intraperitoneal administration of graded doses of the test compound. The animals' survival time in a temperature-controlled hypoxic environment (96% nitrogen and 4% oxygen) is recorded. A statistical comparison is made between coincident vehicle treated animals and the experimental group. The dose-response and minimum active dose (MAD) for compounds are obtained [A A Artu and J D Michenfelder, Anaesthesia and Analgesia, 1981, 60, 867]. Other modes of administration can also be used.

e) Antiepileptic activity may be measured by assessing a compound's ability to prevent the hind limb tonic extension component of the seizure in groups of mice or rats induced by maximal electroshock (MES) after oral, intraperitoneal, intravenous or subcutaneous administration, according to the procedures of the Epilepsy Branch, NINCDS as published by R J Porter, et al, Cleve Clin Quarterly 1984, 51, 293, and compared with the standard agents dilantin and phenobarbital.

f) The 4-vessel occlusion (4-VO) model of stroke is used to produce global ischaemia in the rat and is an essential technique to evaluate the effectiveness of compounds to prevent damage to areas of selective vulnerability in the brain, notably the CA1 pyramidal neurons of the hippocampus. This area is involved in the pathways for short term memory formation in both laboratory animals and humans. The procedure consists of cauterizing the vertebral arteries and isolating the carotid arteries of rats maintained under anaesthesia on day 1. On day 2 the carotids are clamped for varying periods of time, ten minutes is sufficient to destroy the CA1 neurons. The clamps are removed, reflow initiated and drugs administered at various times post reflow. Body temperature is maintained at 37° C. throughout the ischaemia and recovery periods. The CA1 neurons die off over a 48–72 hour period and normally the rats are treated for at least 3 days with drug (ip, iv, or po) and at 7 days the brains are removed for histology. Rating of CA1 damage is accomplished using two methods, counting of viable CA1 neurons and scoring of degree of gross pathology [W A Pulsinelli and A Buchan, 'The NMDA receptor/ion channel: Its importance to in vivo ischemia injury to selectively vulnerable neurons', Pharmacology of Cerebral Ischemia, edited by J Krieglstein and H Oberpichler, published by Wissenschafiliche Verlagsgesellschaft, Stuttgart, 1990, p169].

g) In the Focal Model of Stroke, spontaneously hypertensive rats (SHR) are used as experimental subjects because of their relatively poor collateral brain circulation. A 2 hour focal ischemia is achieved in SHR by clamping the middle cerebral artery and the ipsilateral carotid while maintaining anaesthesia. Drugs can be administered (usually ip) either before or at various times after clamping the arteries or when reflow commences at 2 hours. The brains are removed 24 hours after the experiment and frozen, sectioned and drug effects toward reducing infarct volume of the cerebral cortex is determined using a custom-built computer quantification system [A M Buchan, D Xue and A Slivka, Stroke, 1992, 23, 273.]

The toxicity of the compound of the invention may be measured in the following tests.

a) Dose ranging studies based on those described by N W Spurling and P F Carey, 'A protocol for dose selection in repeat dose toxicity studies', poster presentation 974 at the Society of Toxicology annual meeting, Seattle, USA, 23–27 February, 1992. Rats are dosed intravenously daily with progressively increasing doses of test compound until a maximum repeatable dose is found above which the incidence of convulsions and other abnormal clinical signs is unacceptable.

b) The inverted screen test [L L Cougenour, J R McLean, and R B Parker, Pharmacol Biochem Behav, 1977, 6, 351]. Mice are dosed with test compound and 30 minutes later are placed on a small wire platform which is inverted through an arc of 180°. Mice unable to climb to the upright position within 30 seconds are rated as failures. Using sufficient doses and numbers of animals an appropriate $TD_{50}$ (dose in which 50% fail) can be determined readily.

c) The observation test for 28 behavioral signs according to S Irwin [Psychopharmacology 1968, 13, 222]. Groups of 3 mice per dose are administered incremental amounts of test compound in the range 25–400 mg/kg and observed for 28 symptoms immediately after dosing, 30 minutes, 3 hours and 24 hours post dose.

d) Test for Phencyclidine (PCP)-Like Behaviour. PCP-like behaviours are a side effect of potent competitive and non-competitive NMDA receptor antagonists. In a screen to determine whether a compound possesses this liability, rats are dosed orally with test compound (expressed as multiples of the oral $ED_{50}$ for protection in the MES test) and placed into individual clear plastic cages and observed over a 4 hour period for any incidence of 5 characteristic behaviours associated with PCP, namely hyperactivity, ataxia, circling, head weaving and retropulsion. Five rats per treatment group are observed and compared to a control group receiving PCP. A total incidence score would be 25, i.e. 5 rats exhibiting all 5 behaviours. PCP at 10 times the $ED_{50}$ produces a score of 25 [W Koek, J H Woods, P Ornstein, 1987, Psychopharmacology, 91, 297].

e) Gang Plank Escape Test to measure neural impairment in rats [G E Garske et al, Epilepsy Research, 1991, 9, 161 ]. Rats are placed on a narrow board ( 1.25 cm wide suspended 40 cm above the bench top) in a well lit entry cubicle which enters a progressively darkened box connected to a dark escape cubicle at the other end (board is 63 cm long). A rat is impaired if it fails to negotiate the plank. The task takes into account two known behaviours of rats, i.e. fear of height and seeking a dark environment.

Linear pharmacokinetics may be detected in rats by evaluating the area under the plasma concentration v time curves obtained upon single intravenous administration of test compound at increasing doses (Smith et al, Xenobiotica, 20, 1187–1199, 1990).

Blood was removed from a jugular vein catheter at various times over a 24 hour period. The plasma was separated by centrifugation and the concentration of test compound was determined using HPLC-UV chromatography. The plasma concentration v time values were plotted for each dose and the area under each curve estimated. Where linear pharmacokinetics are present, the area under the plasma concentration v time curve for a given dose is directly proportional to the dose administered. A finding of linear pharmacokinetics in rats indicates that linear pharmacokinetics would be found in humans (Leander et al, Epilepsia, 33,696–704, 1992, at p703).

According to another aspect of this invention there is provided a method of treatment of a neurodegenerative disorder, which comprises administering a therapeutically and/or anti-neurodegenerative effective amount of a compound of the invention to a patient. Of particular interest is such a method in which the dose of the compound administered is linearly proportional to the blood plasma concentration of the compound desired.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of the invention may be used on their own or in the form of appropriate medicinal preparations for enteral or parenteral administration. According to a further aspect of the invention, there is provided a pharmaceutical composition comprising preferably less than 80% and more preferably less than 50% by weight of a compound of the invention in admixture with a pharmaceutically acceptable adjuvant, diluent or carrier.

Examples of diluents and carriers are:

for tablets and dragees: lactose, starch, talc, stearic acid;

for capsules: tartaric acid or lactose;

for injectable solutions: water, alcohols, glycerin, vegetable oils;

for suppositories: natural or hardened oils or waxes.

An adjuvant of particular interest when the compound of the invention is to be used in the treatment of Parkinson's disease is L-dopa.

According to a further aspect of the invention, there is provided the use of a compound of the invention as active ingredient in the manufacture of a medicament for the treatment of a neurodegenerative disorder.

The compounds of the invention may also have the advantage that they are less toxic, more efficacious, are longer acting, have a broader range of activity, are more potent, produce fewer side effects, are more easily absorbed or have other useful pharmacological properties, than compounds previously indicated in the therapeutic fields mentioned above.

The invention is illustrated by the following examples.

EXAMPLE 1

Preparation of (S)-α-phenyl-2-pyridineethanamine dihydrochloride a) α-Phenyl-2-pyridineethanamine dihydrochloride To a cooled (0° C.) solution of benzaldehyde (34.24 g, 0.323 moles) in 600 ml of tetrahydrofuran (THF) was added lithium bis(trimethylsilyl)-amide (LHMDS) (323 ml of a 1.0M solution in THF, 0.323 moles) dropwise over 30 minutes. This mixture was stirred at 0° C. for three hours.

In a separate round bottom flask containing a cooled (−78° C.) solution of 2-picoline (30.0 g, 0.323 moles) in THF (600 ml) was added n-butyllithium (n-BuLi) (129.2 ml of a 2.5M solution in hexane) over twenty minutes.

The first reaction mixture was allowed to warm to 0° C. and remain there for an additional forty minutes. The second reaction mixture (containing the lithiated anion of 2-picoline) was cannulated into the first reaction mixture over 20 minutes. After 30 additional minutes the cold bath was removed and the mixture was allowed to warm to ambient temperature. After an additional one hour, the reaction mixture was poured into a separating funnel charged with ice (11) and 12N HCl (200 ml). The aqueous layer was washed with 3×200 ml of diethyl ether ($Et_2O$) and then basified with 25% NaOH solution in water. The aqueous layer was extracted with 2×200 ml of chloroform, the chloroform extracts dried over $MgSO_4$, filtered and concentrated in vacuo. The residue was dissolved in ethyl acetate (EtOAc) and acidified with a saturated solution of HCl/EtOAc. The solution was diluted with $Et_2O$ and the resulting white solid filtered and dried in vacuo to give the subtitle compound (37.08 g, 43%), mp= 206°–208° C.

b) (S)-α-Phenyl-2-pyridineethanamine dihydrochloride

To a solution of racemic α-phenyl-2-pyridineethanamine (the free base of the product of step (a), obtained by neutralizing an aqueous solution of the product of step (a) with a 25% NaOH solution in water and extracting with chloroform) (10.96 g, 0.0553 moles) in EtOAc (400 ml) was added a solution of S(+)-mandelic acid (8.41 g, 0.0553 moles) in EtOAc (300 ml). The resulting precipitate was recrystallized from hot EtOAc (500 ml) an additional three times. The salt was basified with a 25% NaOH solution in water, extracted with 3×100 ml of chloroform, dried over $MgSO_4$, filtered and concentrated in vacuo. The residue was dissolved in EtOAc (300 ml) and acidified with a saturated solution of HCl/EtOAc. The resulting white solid was filtered and dried in vacuo to give (−)-α-phenyl-2-pyridineethanamine dihydrochloride (5.5 g), mp=220°–222° C., $[\alpha]_D$= −87.3° (c= 1.0, $CH_3OH$).

The filtrate from the initial precipitation was neutralized with 25% NaOH solution in water, extracted with 2×250 ml of $CHCl_3$, dried over $MgSO_4$, filtered and concentrated in vacuo. The residue was dissolved in EtOAc (500 ml) and to this solution was added a solution of R(−)-mandelic acid (6.5 g, 0.043 moles) in EtOAc (500 ml). The precipitate was filtered off and recrystallized an additional three times. The salt was basified with 25% NaOH solution in water, extracted with 3×100 ml of chloroform, dried over $MgSO_4$, filtered and concentrated in vacuo. The residue was dissolved in EtOAc (300 ml) and acidified with a saturated solution of HCl/EtOAc. The resulting white solid was filtered and dried in vacuo to give the title compound (3.84 g), mp=220°–222° C., $[\alpha]_D$=+87.1° (c=1.1, $CH_3OH$).

The enantiopurity may be determined by derivatizing either the mandelic acid or dihydrochloride salt with enantiopure (greater than 99.5%) methylbenzyl isocyanate, and then analyzing by HPLC using a normal phase column with ethanol/hexane [6:94] as solvent. The enantiopurity of the enantiomers obtained above was shown to be greater than 99.5%.

X-ray crystallography showed the (+)-enantiomer to have (S)-absolute stereochemistry.

EXAMPLE 2

Preparation of (S)-α-phenyl-2-pyridineethanamine (S)-malate from (S)-α-phenyl-2-pyridineethanamine dihydrochloride To a solution of 3.0 g of the title compound of Example 1 in 100 ml of ethyl acetate was added a saturated solution of (S)-malic acid (99%, Aldrich Chemical Company Limited, >99.8% enantiopure as determined by chiral HPLC) in ethyl acetate until the resulting mixture became acidic. The resulting precipitate was dissolved by the addition of methanol and precipitated by the addition of ether. The resulting white solid was filtered off, and dried in vacuo to yield 3.85 g of the title compound, mp=134°–136° C., $[\alpha]_D$=51.02° (c=0.9957, $CH_3OH$, 23° C.); enantiopurity of the amine moiety >99.999% (as determined by chiral HPLC).

EXAMPLE 3

Preparation of (S)-α-phenyl-2-pyridineethanamine (S)-malate from α-phenyl-2-pyridineethanamine dihydrochloride A solution containing 5.95 g (30.1 mmole) of the compound of Example 1(a) and 4.8 g (35.8 mmole) of (S)-malic acid (99%, Aldrich Chemical Company Limited, >99.8% enantiopure as determined by chiral HPLC) in a total of 250 ml of acetone was heated until all solids had dissolved, a small amount of methanol was required to effect complete dissolution. The solids that formed upon cooling were collected and recrystallized twice from 250 ml of hot acetone, again a small amount of methanol was required to effect complete dissolution. The resulting product was collected and dried in vacuo to yield 2 g of the title compound, $[\alpha]_D$=+50.03° (c=0.9563, $CH_3OH$, 23° C.); enantiopurity of the amine moiety=99.8% (as determined by chiral HPLC).

EXAMPLE 4

The stability of the title compound of Example 1 and (S)-α-phenyl-2-pyridineethanamine (S)-malate to moisture was investigated. The former compound was found to deliquesce at a relative humidity of 80%, whereas the latter compound absorbed only 0.1% of its own weight of water at the same relative humidity.

EXAMPLE 5

The title compound of Example 1 was found to have an activity ($ED_{50}$) of 3.7 mg/kg in the prevention of hind limb tonic extension in rats induced by maximal electroshock (MES) (described above) when administered orally. Its enantiomer had an $ED_{50}$ of 20.2 mg/kg.

EXAMPLE 6

Preparation of (S)-α-phenyl-2-pyridineethanamine benzoate from (S)-α-phenyl-2-pyridineethanamine dihydrochloride To a solution of the title compound of Example 1 (7.8 g) in ethylacetate (20 ml) was added benzoic acid (4.7 g) in hot ethyl acetate (40 ml). The mixture was allowed to cool to ambient temperature and stirred for one hour. The resulting white solid was filtered off, washed with ethyl acetate and dried in vacuo to yield the title compound (10.4 g). mp=134°–136° C; $[\alpha]_D$=+47.78° (c=1.02965, $CH_3OH$, 23° C.); enantiopurity of the amine moiety 99.8% (as determined by chiral HPLC).

EXAMPLE 7

The stability of the title compound of Example 1 and the title compound of Example 6 to moisture was investigated. The former compound was found to deliquesce at a relative humidity of 80%, whereas the latter compound had not started to deliquesce at a relative humidity of 97%.

What is claimed is:

1. (S)-α-phenyl-2-pyridineethanamine, which is greater than 90% enantiopure, and pharmaceutically acceptable derivatives thereof.

2. (S)-α-phenyl-2-pyridineethanamine, which is greater than 99% enantiopure, and pharmaceutically acceptable derivatives thereof.

3. (S)-α-phenyl-2-pyridineethanamine, and pharmaceutically acceptable derivatives thereof.

4. A pharmaceutical formulation including (S)-α-phenyl-2-pyridineethanamine as defined in any one of claims 1 to 3, or a pharmaceutically acceptable derivative thereof, in admixture with a pharmaceutically acceptable adjuvant, diluent or carrier.

5. A method of treatment of a neurodegenerative disorder, selected from the group consisting of epilepsy, stroke, cerebral ischacmia and anoxia which comprises administering an NMDA blocking, antihypoxia, antiepileptic or antiischemic effective amount of (S)-α-phenyl-2-pyridineethanamine, as defined in any one of claims 1 to 3, or a pharmaceutically acceptable derivative thereof, to a patient.

6. A method of treatment as claimed in claim 5, wherein the dose of the compound administered is linearly proportional to the blood plasma concentration of the compound desired.

7. (S)-α-phenyl-2-pyridineethanamine (S)-malate which is greater than 90% enantiopure.

8. (S)-α-phenyl-2-pyridineethanamine (S)-malate which is greater than 99% enantiopure.

9. (S)-α-phenyl-2-pyridineethanamine (S)-malate.

10. A pharmaceutical formulation including (S)-α-phenyl-2-pyridineethanamine (S)-malate as defined in any one of claims 7 to 9, in admixture with a pharmaceutically acceptable adjuvant, diluent or carrier.

11. A method of treatment of a neurodegenerative disorder, selected from the group consisting of epilepsy, stroke, cerebral ischaemia and anoxia which comprises administering an NMDA blocking, antihypoxia, antiepileptic or antiischemic effective amount of (S)-α-phenyl-2-pyridineethanamine (S)-malate, as defined in any one of claims 7 to 9, to a patient.

12. A method of treatment as claimed in claim 11, wherein the dose of the compound administered is linearly proportional to the blood plasma concentration of the compound desired.

13. (S)-α-phenyl-2-pyridineethanamine benzoate which is greater than 90% enantiopure.

14. (S)-α-phenyl-2-pyridineethanamine benzoate which is greater than 99% enantiopure.

15. (S)-α-phenyl-2-pyridineethanamine benzoate.

16. A pharmaceutical formulation including (S)-α-phenyl-2-pyridineethanamine benzoate as defined in any one of claims 13 to 15, in admixture with a pharmaceutically acceptable adjuvant, diluent or carrier.

17. A method of treatment of a neurodegenerative disorder, selected from the group consisting of epilepsy, stroke, cerebral ischacmia and anoxia which comprises administering an NMDA blocking, antihypoxia antiepileptic or antiischemic effective amount of (S)-α-phenyl-2-pyridineethanamine benzoate as defined in any one of claims 13 to 15, to a patient.

18. A method of treatment as claimed in claim 17, wherein the dose of the compound administered is linearly proportional to the blood plasma concentration of the compound desired.

* * * * *